United States Patent [19]

Maclay et al.

[11] 4,315,937

[45] Feb. 16, 1982

[54] ERGOTS AND THEIR USE IN TREATING MINIMAL BRAIN DYSFUNCTION

[75] Inventors: William P. Maclay, Farnborough; Mackenzie G. Wallace, Hatfield, both of England

[73] Assignee: Sandoz Ltd., Basel, Switzerland

[21] Appl. No.: 210,695

[22] Filed: Nov. 26, 1980

[30] Foreign Application Priority Data

Nov. 28, 1979 [GB] United Kingdom ............... 41095/79
Mar. 21, 1980 [GB] United Kingdom ............... 10762/80

[51] Int. Cl.$^3$ .................... A61K 31/48; A61K 31/475
[52] U.S. Cl. ..................................... 424/261; 424/262
[58] Field of Search ................................. 424/261, 262

[56] References Cited

U.S. PATENT DOCUMENTS

| | | | |
|---|---|---|---|
| 3,160,562 | 12/1964 | Cerletti et al. | 424/261 |
| 3,218,324 | 11/1965 | Hoffman et al. | 424/261 |
| 3,849,562 | 11/1974 | Richardson | 424/261 |
| 3,883,655 | 5/1975 | Fuxe | 424/261 |
| 3,966,923 | 6/1976 | Serre | 424/261 |
| 3,987,173 | 10/1976 | Borreda | 424/261 |

*Primary Examiner*—Stanley J. Friedman
*Attorney, Agent, or Firm*—Gerald D. Sharkin; Robert S. Honor; Thomas O. McGovern

[57] ABSTRACT

Ergots are described which are useful in the treatment of minimal brain dysfunction in children. A particularly useful compound is co-dergocrine.

7 Claims, No Drawings

ERGOTS AND THEIR USE IN TREATING MINIMAL BRAIN DYSFUNCTION

This invention relates to a new use of ergots and pharmaceutical compositions therefor.

It has now been found that certain ergots are useful in the treatment of minimal brain dysfunction in children, e.g. of biological age from 5 to 13 years, as indicated in clinical trials. Minimal brain dysfunction is characterized e.g. by hyperactivity and impaired coordination or in some cases hypoactivity and listlessness; short attention span, poor concentration ability and impaired learning ability; low frustration tolerance and antisocial behaviour; impaired sphincter control (e.g. enuresis); resistance to social demands, lability, altered reactivity, increased agressiveness and dysphoria (c.f. for example WENDER, Minimal Brain Dysfunction in Children; WILEY-INTERSCIENCE 1971). The compounds concerned are those of formula

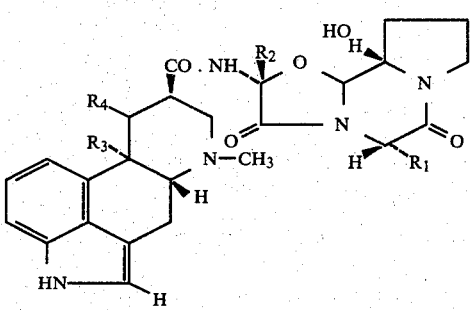

wherein
$R_1$ is isopropyl, isobutyl, sec.butyl or benzyl,
$R_2$ is methyl, ethyl or isopropyl,
$R_3$ and $R_4$ are each hydrogen, or
$R_3$ and $R_4$ together are a single bond.

Such compounds include dihydroergocornine, dihydroergocristine, dihydro-α-ergocryptine, dihydro-β-ergocryptine or a mixture of approximately equal proportions by weight of (a) dihydroergocornine, (b) dihydroergocristine, and (c) α- and β-dihydroergocryptine in a 2:1 weight ratio, such as ergoloid mesylates, ergotamine, dihydroergotamine, dihydroergonine.

METHODS AND RESULTS OF CLINICAL TRIALS USING ERGOLOID MESYLATES

Seven children aged between 7 and 11, mean age 9.9 years, were selected using the WHO multi-axial descriptive diagnostic classification. The subjects were drawn from special classes for "slow learners" in the local National Junior Schools and had concentration difficulties which were either constitutional or due to various types of development lag, but were neither mentally handicapped nor neurotically withdrawn.

Those selected had a clinical history taken and their height recorded. They are assessed on the Wechsler Intelligence Scale for children (WISC) and their Reading Age recorded. All subjects fell within the range of average intellectual function. The Test Battery comprised a Rotary Pursuit (RP) task (which assessed time on target); Electromyographic Response (EMG); Digital Blood Volume (DBV), assessed photoplethysmographically; and Digital Skin Temperature.

In addition, the Bristol Social Adjustment Guides (BSAG) and an assessment of hyperactivity were completed by class teachers and parents. A Social Worker was employed to make regular visits to the subjects, parents and teachers to ensure that the rating scales were completed and to check drug compliance. All subjects were given matching placebo, half tablet twice daily for three weeks followed by one week active treatment, half tablet (0.75 mg) twice daily. The dose was subsequently increased to one tablet (1.5 mg) twice daily for a further 5 weeks. The tests battery was administered at baseline and at 3, 6 and 9 weeks.

Details of the subjects are given in the following Table 1.

TABLE 1

| Subject | Age | Sex | Height (Inches) | Weight (kgs) | I.Q. | Reading Age |
|---|---|---|---|---|---|---|
| 1 | 7.9 | F | 49½ | 23½ | 105 | 6.6 |
| 2 | 9.6 | M | 54 | 28½ | 109 | 8.0 |
| 3 | 9.9 | F | 52¾ | 39½ | 103 | 6.6 |
| 4 | 10.0 | M | 55½ | 33½ | 100 | 7.7 |
| 5 | 10.3 | M | 52 | 25 | 99 | 6.5 |
| 6 | 10.5 | M | 52½ | 28 | 101 | Not recorded |
| 7 | 11.7 | M | 58½ | 37½ | 104 | 9.1 |

They were of average height and I.Q., but their reading ages were from 1½ to 3 years below normal for children in the social group. They came from stable homes and were the children of semi-skilled workers. Two of the five children were not allowed to complete the study and were lost to follow up.

The dosage regime was altered during the study as within four days of increasing the medication from 0.75 mg b.d to 1.5 mg b.d three of the families reported that the children became increasingly irritable, short tempered, ill-humoured and seemed to be brooding with great intensity. In view of this the dosage was reduced to 0.75 mg b.d for the whole group.

The results show changes in all areas tested at both drug levels, the assessments at week 6 reflect changes when the dose was increased while those at week 9 reflect changes after the dose was reduced to the previous level. Greater changes in the EMG response, the DBV and the RP task occurred at week 6, while changes in DST were greatest at week 9. These changes were shown in Table 2.

TABLE 2

| Observation | BASELINE | WEEK 3 (PLACEBO) | WEEK 6 (0.75mg → 1.5mg) | WEEK 9 (0.75 mg) |
|---|---|---|---|---|
| ELECTROMYOGRAPHIC[1] RESPONSE | 899.8 | 748.6 | 878.8 | 757.3 |
| DIGITAL BLOOD VOLUME[2] | 217.6 | 217.6 | 269.2 | 245.1 |
| DIGITAL SKIN TEMPERATURE[3] $O_c$ | 21.9 | 28.6 | 26.9 | 30.0 |
| ROTOR PURSUIT TASK TIME ON TARGET PER 60 SECS. | 29.9 | 30.4 | 36.8 | 32.3 |
| ROTOR PURSUIT TASK ERRORS PER 60 SECS. | 61.4 | 63.6 | 57.6 | 58.0 |

TABLE 2-continued

| Observation | BASELINE | WEEK 3 (PLACEBO) | WEEK 6 (0.75mg → 1.5mg) | WEEK 9 (0.75 mg) |
|---|---|---|---|---|
| BRISTOL SOCIAL ADJUSTMENT GUIDE | | | | |
| OVERALL ADJUSTMENT SCORE | 11.6 | 10.5 | 9.5 | 8.8 |

Comments on Table 2

(1) The EMG response was that of total EMG activity occurring over a 20 second period. This was an absolute measure in microvolt seconds (area under the curve). The subjects were sampled at 10×1 second periods over the 20 seconds.
(2) Digital Blood Volume was measured over 20 seconds taken at one observation per second in unit measurements.
(3) Skin temperature was measured once per second over 20 seconds and is an absolute measure.

The results showed:
1. Electromyographic values increased which signifies increased muscle tension/activity. This could be a reflection of increased mental alertness.
2. Increased digital blood volume.
3. Improved performance in reaction time test. The change in values in the above all reached levels of statistical significance of at least $p<0.5$.
4. Teachers reported improvement in the Bristol Social Adjustment Guides.
5. Parents reported improvement (subjective statements).
6. A definite drug effect.

From the results obtained there was no noticeable effect al all during the placebo run-in period, but there was a noticeable effect as soon as active treatment was commenced. Thus, the clinical findings show that none of the parents or children reported any changes during the placebo phase, but within 10 days of commencing active treatment (0.75 mg b.d) all concerned remarked on the development of a good humoured and more conscientious approach to work both at school and at home.

Families commented on the decreased bickering and fighting with both siblings and parents during homework. The two eneuretic children became dry and have remained so.

Following the planned dosage increase side effects were reported. One child spent increasing time studying his homework intensely and became very frustrated at not being able to "take it in". Two children became confused and were unable to hold a conversation, and one of them had been given a double dose by the parents in error on the day of his confusion. This state lasted some 24 hours after the last dose, but all three children were very much better 12 hours later and quite normal within 48 hours. All children resumed their previous good humoured approach to school and homelife after reducing the dose to 0.75 mg b.d.

For the new use the dosage will, of course, vary depending on the compound employed, mode of administration and treatment desired. However, in general, satisfactory results are obtained when administration at a daily dosage of from about 1 mg to about 20 mg, conveniently given in divided doses 2 to 4 times a day or in sustained release form. In the case of ergoloid mesylates, the preferred total daily dosage is in the range from about 1 to about 3 mg especially up 1 to 1.5 mg.

The compound may be administered in free base form or in pharmaceutically acceptable acid addition salt form, e.g. the hydrochloride or mesylate.

The compound may be administered orally in the form of tablets, powders, granules, capsules, suspensions, syrups and elixirs, or parenterally in the form of injectable solutions or suspensions. Oral administration is preferred. Aside from the compound the preparation may contain pharmaceutically inert organic or inorganic adjuvants, optionally granulating agents, binding agents, lubricants, dispersing agents, wetting agents and preservatives. Moreover, the pharmaceutical preparations may contain colouring, flavouring and sweetening substances, etc. Adjuvants for the production of tablets may be calcium carbonate, lactose, microcrystalline cellulose may be used as granulating and disintegrating agents, starch, polyvinylpyrrolidone and gelatine may be used as binding agents, and magnesium stearate, stearic acid and talc as lubricants. Tablet formulations may be coated. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound on its own or together with an inert solid diluent, for example calcium phosphate, starch, mannitol, and microcrystalline cellulose.

Solid preparations are preferred, especially hard-filled capsules and tablets, for reasons of easier production and favourable administration.

By way of example the following compositions may be used in the method of the invention.

EXAMPLE 1: Dihydroergotamine tablets

Each tablet contains:

| Dihydroergotamine mesylate | 1.015 | mg |
|---|---|---|
| Tartaric acid | 0.1 | mg |
| Lactose (pulverized) | 84.985 | mg |
| Corn starch | 8.00 | mg |
| Gelatine | 0.3 | mg |
| Magnesium stearate | 0.5 | mg |
| Stearic acid | 1.1 | mg |
| Talc | 4 | mg |

EXAMPLE 2: Ergoloid mesylates tablets

Each tablet contains:

| Ergoloid mesylates | 1.015 | mg |
|---|---|---|
| Stearic acid | 2 | mg |
| Polyvinylpyrrolidone | 4 | mg |
| Talc | 4 | mg |
| Corn starch | 8 | mg |
| Lactose | 140.985 | mg |

If desired tablets may be made with 0.25 mg or 1.5 mg of ergoloid mesylates in analogous manner.

What we claim is:

1. A method of treating minimal brain dysfunction in children which comprises administering to a child having the minimal brain dysfunction a therapeutically effective dose of (i) a compound of formula I

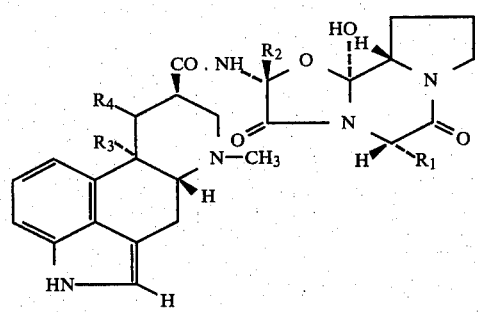

wherein $R_1$ is isopropyl, isobutyl, sec.butyl or benzyl, $R_2$ is methyl, ethyl or isopropyl, $R_3$ and $R_4$ are each hydrogen, or $R_3$ and $R_4$ together are a single bond, or a pharmaceutically acceptable acid addition salt thereof; or (ii) a mixture of approximately equal proportions by weight of (a) dihydroergocornine, (b) dihydroergocristine and (c) α- and β-dihydroergocryptine in a 2:1 weight ratio in free base or pharmaceutically acceptable acid addition salt form.

2. A method according to claim 1 wherein the compound of the formula I is selected from dihydroergocornine, dihydroergocristine, dihydro-α-ergocryptine, dihydro-β-ergocryptine, ergotamine, dihydroergotamine or dihydroergonine, or a pharmaceutically acceptable acid addition salt thereof.

3. A method according to claim 1 in which a therapeutically effective amount of a mixture of approximately equal proportions by weight of (a) dihydroergocornine, (b) dihydroergocristine and (c) α- and β-dihydroergocryptine in a 2:1 weight ratio in free base or pharmaceutically acceptable acid addition salt form is administered to the child.

4. A method according to claim 3 in which the mixture is ergoloid mesylates.

5. A method according to claim 1 in which 1 to 20 milligrams of the active agent are administered daily.

6. A method according to claim 3 in which 1 to 3 milligrams of the mixture are administered daily.

7. A method according to claim 4 in which 1 to 1.5 milligrams of the ergoloid mesylates are administered daily.

* * * * *